United States Patent
Rush et al.

(10) Patent No.: US 7,717,560 B2
(45) Date of Patent: May 18, 2010

(54) EYE-ADMINISTERED, MOVING-IMAGE PHYSIOLOGIC TEST SYSTEM AND METHOD

(76) Inventors: John B. Rush, 95386 Mountain Rd., Gold Beach, OR (US) 97444; Dustin J. Rush, 9267 SW. Second Ave., Portland, OR (US) 97219

( * ) Notice: Subject to any disclaimer, the term of this patent is extended or adjusted under 35 U.S.C. 154(b) by 397 days.

(21) Appl. No.: 11/906,643

(22) Filed: Oct. 3, 2007

(65) Prior Publication Data
US 2009/0091707 A1    Apr. 9, 2009

(51) Int. Cl.
*A61B 3/08*    (2006.01)
*A61B 3/02*    (2006.01)
(52) U.S. Cl. ...................... 351/201; 351/223
(58) Field of Classification Search ........... 351/200, 351/201, 222, 223, 237, 239, 240, 243
See application file for complete search history.

(56) References Cited

U.S. PATENT DOCUMENTS
6,517,204 B1 * 2/2003 Ghahramani ............... 351/201

* cited by examiner

*Primary Examiner*—Jack Dinh
(74) *Attorney, Agent, or Firm*—Jon M. Dickinson, PC; Robert D. Varitz, PC

(57) ABSTRACT

A physiologic test, and a system for implementing this test, including, from a methodologic point of view, (a) illuminating the central field in a test subject's eye with a relative-motion test image produced on an image display structure by a motion-image-creation structure, (b) by such illuminating, creating a related, subject-perception image, (c) requesting a subject report describing the observed presence and nature, if any, of a distortion, relative to the test image, in the perception image, and (d) thereafter utilizing such a report to assess a test subject's physiologic condition involving macular, paramacular, and neural-pathway physiologic degeneration. A preferred test image, which is fully adjustable by a test administrator with respect to substantially all of its image parameters, takes the form of an image field of elongate, spaced, parallel lines, having edges which distinctly contrast with a background field, and which move smoothly and linearly across the image field.

3 Claims, 3 Drawing Sheets

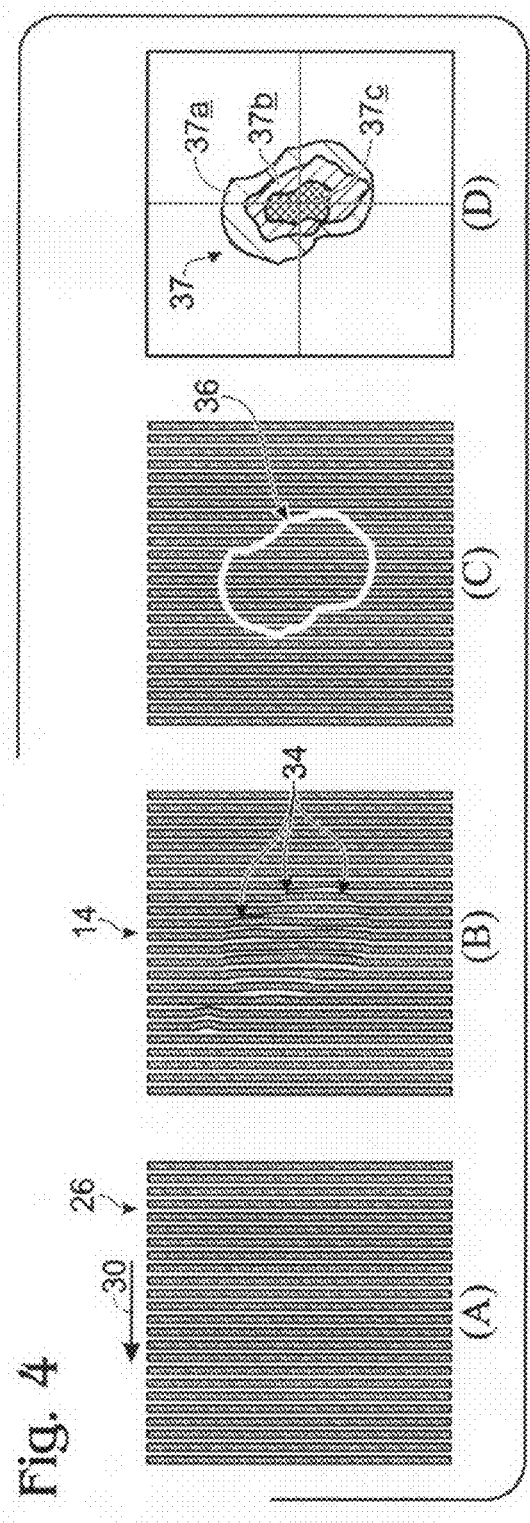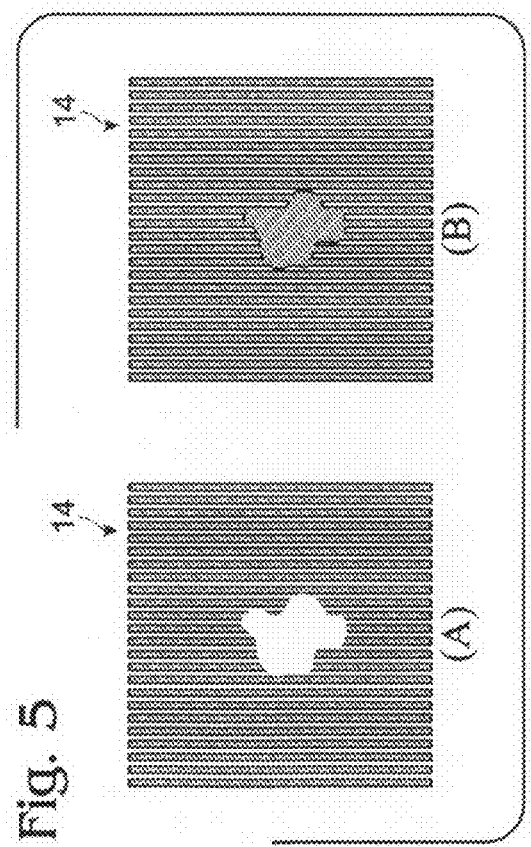

EYE-ADMINISTERED, MOVING-IMAGE PHYSIOLOGIC TEST SYSTEM AND METHOD

BACKGROUND AND SUMMARY OF THE INVENTION

Figure 1:
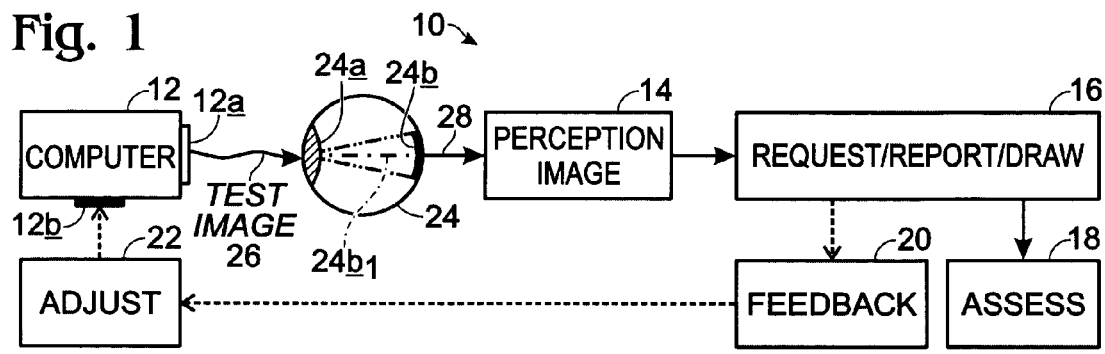

We have recently discovered that certain important physiologic conditions associated with vision, including very early degradation stages of macular metabolic condition, and/or of related neuron-path malfunction, may be detected through the implementation of a simple and easily applied eye test using a special form of moving-pattern, or moving-element, image projected onto an eye's central field to illuminate that field.

The present invention involves that discovery, and relates to features of and in a system and a methodology for implementing the discovery.

Specifically what we have learned is that when the central field of the eye in a subject, also referred to herein as a test subject, is illuminated with certain, predetermined, defined-configuration motion imagery, a patient's perception of this imagery may possess a patient-reportable distortion—a change in the perception image in relation to the source projection image, which change is interpretable specifically to indicate malfunctioning, and especially early-stage malfunctioning, of the macula/paramacula and/or the associated neural pathways. Experimental testing of this methodology has established, as suggested above, its capability for furnishing early warnings about (indications of) degradations in the physiologic condition of these two, vision-communication structures—degradations which are clearly associated with the health of an eye and of the eye's associated communication to the brain.

More specifically, our invention is based upon the discovery that a specially-controlled moving test image (a source image) of spaced, contrasting, alternately light and dark lines which is caused to impinge/illuminate the central field in a person's eye may generate, for the person who's eye is being tested, a changed or distorted perceived, or perception, image possessing an image-regional distortion, or change, that appears to be based effectively upon a time delay in the communication to the brain of a portion (typically within the macula) of the central field which is illuminated by the test image.

In the disclosure of the present invention herein, the term "central field" is employed to refer to the collected structures of the macula and the paramacula in an eye. This central field, which is generally circular in perimetral outline, will be referred to as having a central axis that, essentially, may be visualized as being an axis of revolution of the central-field outline. The neural pathways which are referred to herein are to be understood as being those communication pathways that extend between (a) the structural elements which make up the central field, and in particular, those which make up the macula/paramacula, and (b) the brain.

The term "macula" herein should be understood to include reference to the paramacula.

The term "illuminating", etc., also referred to as "impinging", etc., refers to placing a test image onto an eye's central field. Such an image is referred to herein as possessing a predetermined, stable spatial configuration, and this phraseology is intended to refer to a source test image which, while being selectively adjustable to possess different specific characteristics, has a "stability", or consistency, with regard to those characteristics in relation to its being directed onto, to illuminate, an eye's central field.

The term "perception image", etc., refers herein to that image which a test subject "sees" when an eye's central field is illuminated with a stable test image. This perception image may vary from the stable test image by appearing to be changed, or distorted. Such a change, or distortion, will typically have a particular lateral boundary which resides with a particular lateral shape, and a particular position, within the overall perceived field of the illuminating test image.

With regard to the creation, projection, and interpretive use generally of a special, moving test image, practice of the invention, as will be explained below, contemplates allowance for the selective changing and manipulation of various projectable test-image parameters. For each test image employed, the person tested is asked to describe, and preferably also to sketch an outline, and identify the location, of any perceived image distortion. As will be seen, this reported information may be used to characterize and locate an eye's central-field/neural pathways disfunctionality issues. Different test images, as will be mentioned again below, are useful in furnishing "different points of view" regarding any such issues.

Adjustments of and changes in the mentioned test image may also be performed, typically though not necessarily manually, in a kind of feedback manner, based upon a person's reported, perceived image difference or distortion, to effect counteractive changes in the character per se of a new original, source test image—all for the purpose of creating, for the person under test, an end-result perceived image which is deemed, by that person, as exactly as possible to replicate what is understood to be an otherwise "unmodified" (i.e., non-feedback-manipulated) source test image. Thus, and in this context, the invention contemplates allowing for the performance of image-control processing in relation to the generation of a source test image, whereby, as far as the patient (or person)-perceived image is concerned, that image has all previously reported distortion effectively removed from it. This capability of the methodology and systemic structure of this invention allows for the obtaining of quantitative data which is useful in describing and understanding the nature of any macular, and/or related neural pathway, deficiencies that may be responsible for perception-image distortion.

These and other important features and advantages which are attained by the structure and the practice of the present invention will become more fully apparent as the detailed description of the invention which shortly follows below is read in conjunction with the accompanying drawings.

DESCRIPTIONS OF THE DRAWINGS

FIG. 1 is a simplified, block/schematic illustration of a preferred and best-mode form of a physiology-test (visual-test) methodology and system constructed and implemented in accordance with the present invention. It is also an illustration which is readable, as will be explained, to picture a modified form of the invention, wherein feedback information is employed to yield numeric test-result data.

Figure 2:
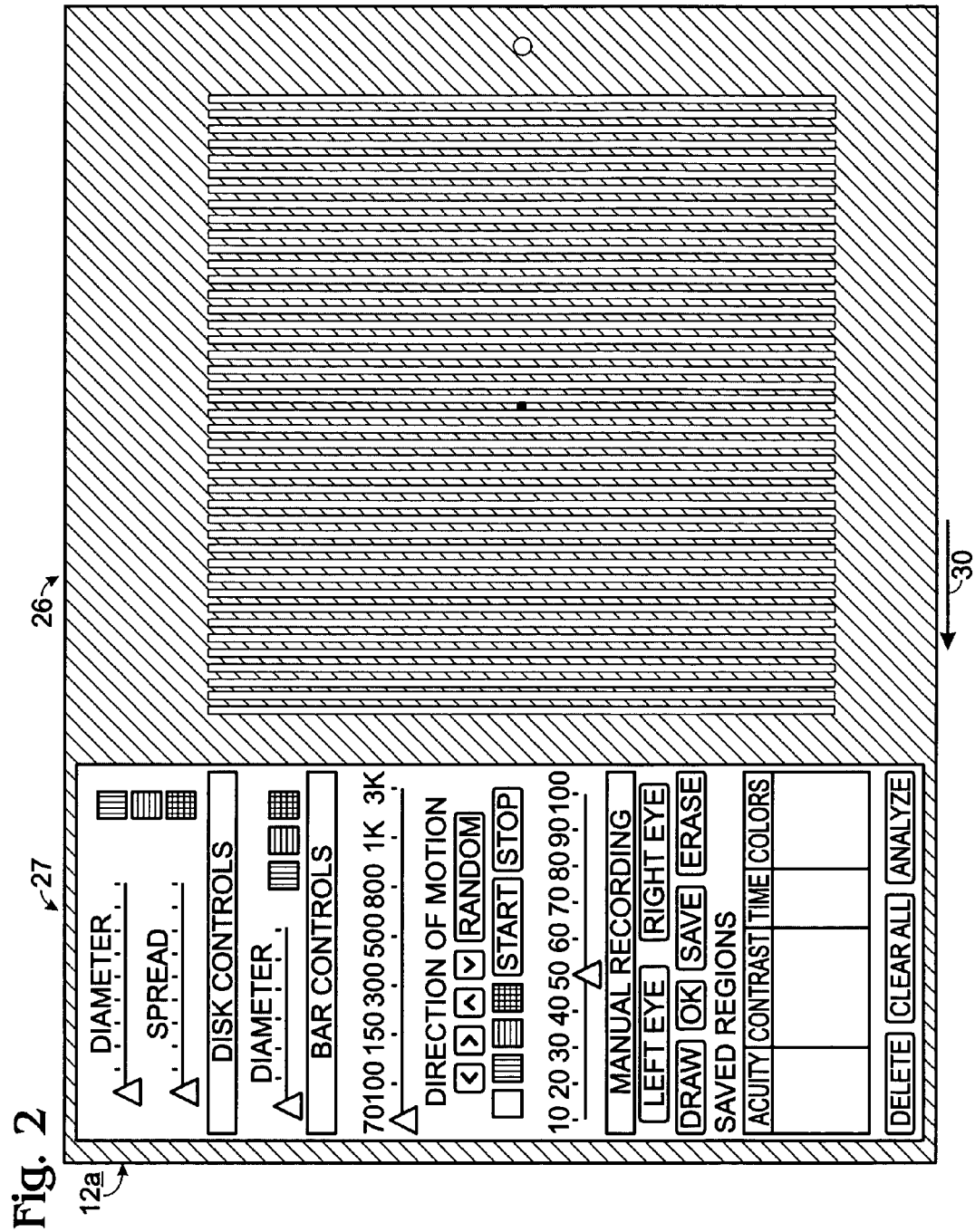

FIG. 2 is an illustration, among other things, of a screen display, such as a computer screen display, of an imagery field (a source test image) employable in the structure and methodology pictured schematically in FIG. 1. This figure specifically illustrates one set of visual imagery components, or elements, which make up one very useful form of an appropriate test-implementing screen display including one characteristic configuration of a moving source test image. This configuration takes the form of a rectangular field containing plural, elongate, spaced, substantially parallel straight lines which present an edge contrast with the background-formed spaces between them.

FIG. 2 also illustrates a representative test-administering, virtual interactive-control structure, or virtual-control structure, which enables manipulation and control by a test administrator of and over various features/parameters of the illustrated test image.

The pictured test image and the virtual-control structure typically will not always appear simultaneously on the illustrated display screen. More will be said about this later herein.

Figure 3:
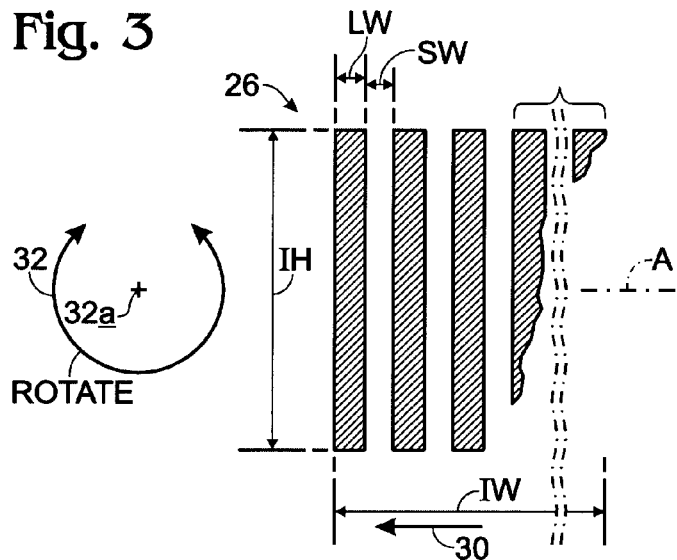

FIG. 3 is a stylized and fragmentary schematic drawing illustrating various operative features/parameters of a moving-straight-line source test image which is featured in one form of practice of the present invention.

FIGS. 4A, 4B, 4C and 4D collectively illustrate several stages, or aspects, of one representative test event implemented in accordance with practice of the present invention.

FIGS. 5A and 5B, when viewed comparatively with FIG. 4B (which shows one form of a perception-image "distortion"), individually and respectively illustrate two additional kinds of perception-image distortions.

Figure 6:
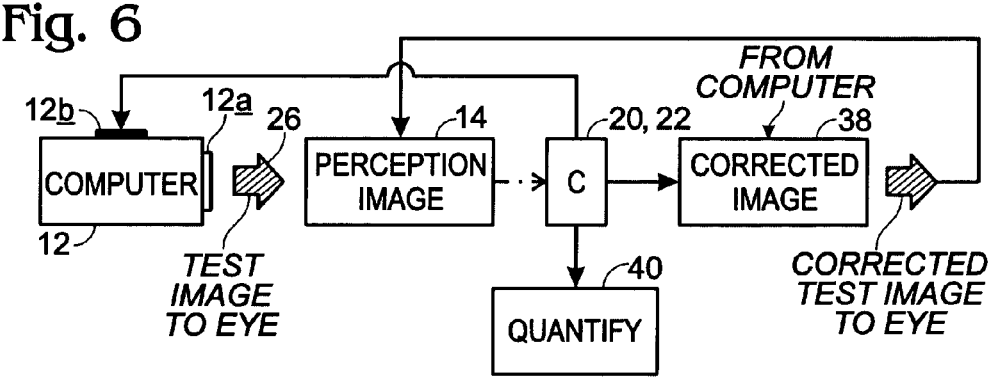

FIG. 6 further illustrates the modified practice of, and structure for, the present invention mentioned above in relation to the description of FIG. 1. This modified practice and structure involve producing feedback adjustments/manipulations typically, though not necessarily manually, in a moving test image—manipulations that are designed to adjust, so as to undistort, a perception image that is detected by an eye being tested. Such an adjusted perception image preferably has consciously removed from it, as nearly as possible, all evidence of distortion. This feedback process allows practice of the invention to yield useful numeric data that relates to physiologic issues.

DETAILED DESCRIPTION OF THE INVENTION

Turning attention now to the drawings, and referring first of all to FIG. 1, indicated generally at 10 is both a system and a methodology, in their respective best-mode and preferred forms, for implementing and practicing the present invention. This FIG. 1 illustration includes six, labeled, rectangular blocks 12, 14, 16, 18, 20, 22 which represent different structures and practices, as will shortly be explained. This figure also includes a circle 24 which represents a human eye. As was mentioned earlier herein, FIG. 1 has been created to illustrate both a preferred, and a modified, form of the invention.

Block 12 herein takes the form of a suitably programmed digital computer, also referred to herein as a motion-image-creation structure. Computer 12 is appropriately coupled to a screen display device shown at 12a, and to a user (administrator) input structure, such as a mouse, shown at 12b. Device 12a, which is also referred to herein as an image-display structure, functions to display on its screen what is called herein a source test image. Device 12b functions to enable user (administrator) input to a test-image virtual-control structure which is selectively presentable also as an image on the screen in device 12a along with a related source test image. This screen displayable virtual-control structure is "engageable" by device 12b to change the parameters of a screen-displayed source test image. When a test is underway, with a test subject gazing at the test image, the virtual-control structure is preferably not displayed on the screen of device 12a. It is returned to visibility on this screen when a test administrator wishes to make a change in the character of a test image.

When the system of the invention is being employed in a test procedure with regard to a subject's eye (circle 24), a source test image, which will be described shortly, and which is represented by a serpentine arrow 26 in FIG. 1, is directed through the eye lens 24a to illuminate, or impinge, the central field 24b in the eye. Such impinging is also referred to herein as test-image-impinging. Central field 24b, which includes, as is well-known to those skilled in the art, the macula, and the paramacula, is generally circular in nature, and can be thought of as possessing a central axis which, in FIG. 1, is represented by a dash-dot line shown at $24b_1$.

Neural pathways that extend between central field 24b and the brain are represented by an arrow 28 in FIG. 1, and it is from central-field communication of information to the brain via these pathways that the brain constructs what is referred to herein as a perception image (block 14) in FIG. 1.

In accordance with practice of this invention, a perception image and a source test image may differ by virtue of changes, and/or distortions, occurring in the perception image. With respect to such a perception image (during a test), a subject is asked (requested) to report the presence, nature and location of any such change or distortion, and effectively, to describe, and/or to draw (as will be explained), an outline of such a change or distortion. Such requesting, reporting and drawing activities are represented by block 16 in FIG. 1.

Block 18 in FIG. 1 represents the making of an assessment or an evaluation of a distortion reported and drawn by a subject, with such an assessment being made by a skilled person, such as a physician, who is administering and/or reviewing the results of a particular eye test. The present invention does not involve any details of these activities.

Blocks 20, 22, and the dashed-line arrows associated therewith, along with the other contents of FIG. 1, represent the previously mentioned modified form of the invention. In this modified condition of the invention, feedback (block 20), such as manual feedback, is utilized to implement an adjustment (block 22) in the source test image for a purpose which will be more fully explained shortly. Such an adjustment is made through the previously mentioned user-interface virtual-control structure (shortly to be discussed) which is accessed by a test administrator via user-interface structure 12b.

FIGS. 2-4, inclusive, provide more specific information relating to the mentioned source test image and a test subject's perception image. While different kinds of source test images may be created and employed, one very useful and preferred test image takes the form of a generally rectangular image field which includes a plurality of elongate, generally straight and substantially parallel image, spaced lines which are caused to move in plural, selectable, defined directions within the image field boundaries. This test image, which is simply represented by serpentine arrow 26 in FIG. 1, is shown more specifically as the mentioned field of elongate lines in FIGS. 2, 3 and 4.

Focusing specifically for a moment on FIG. 2, here what is pictured, on the screen in display device 12a, are two, side-by-side, visual presentations, including a test image 26 which is shown toward the right side of FIG. 2, and an administrator-usable virtual-control structure 27 which is presented toward the left side of FIG. 2. Generally speaking, FIG. 2 is the appearance on the screen of device 12a whenever a test administrator wishes to set/adjust the operative parameters of a test image. During times when a test subject is "in position" gazing with one eye at a test image, control structure 27 is removed from the screen. More will be said about this shortly.

The lines which make up preferred test image 26 sit in an image field which might typically have height and width dimensions each of about 10-cm. As has already been mentioned, these lines are preferably parallel to one another, and are also preferably spaced apart by a line-to-line spacing which is substantially equal to the width of the lines.

In FIG. 3, these various image-field and test-image line dimensions are indicated generally by capital-letter markings. Image-field height is represented by the letters IH, image-field width by the letters IW, individual line width by the letters LW, and inter-line spacing by the letters SW. The length of each line is substantially equal to measurement IH.

Included in the center of the test image, as can be seen in FIG. 2, is a small, selectively size-changeable, central dot which is used to mark the spot in the image where the gaze of an eye should be directed during a test. To the right of the image field is another small, selectively size-changeable, lateral dot which is used during a test (a) to provide feedback to a subject regarding whether he or she is looking (gazing) at the right location in the field of the test image, and (b) to aid in positioning the subject's eye at the appropriate distance from the test image. The correct gaze is achieved when a subject is looking directly at the small, central dot in the test image, and the appropriate distance is established when with such a central-dot gaze, and the lateral dot is not seen in the subject's peripheral vision. This distance is referred to herein as one which defines a proper relative positional association with the marker structure and an associated test image.

Within the test image, and more specifically, within the image field of the test image, the lines smoothly march as a soldier course, at any given moment in time, in a particular direction "across" the image field. For the purpose of illustration herein, these lines march from right to left generally as indicated by arrow 30 in FIGS. 2, 3 and 4A. We have determined mathematically that an appropriate speed of line motion across the image field is a linear function of relative line width (LW) and inter-line spacing (SW) under circumstances where LW=SW, and computer 12 has been programmed to accomplish this. A formula under these circumstances, which is useful to establish motion speed is:

Speed (mm/ms)=0.0012$LW$+0.0025

Accordingly, where LW=SW=~5.29-mm, line speed is approximately 0.00882 mm/ms, or about 8.82-mm/sec.

In terms of selecting and establishing a speed of line motion, it is important that motion created in the test image not introduce nystagmus. We have found that a suitable range for defining line speed is about 4-mm/sec to about 14-mm/sec.

Motion of the image lines takes place preferably along a travel line, such as travel line A in FIG. 3, which travel line lies at an angle to the long axes of the image lines, and most preferably along a travel line which is substantially perpendicular to those axes. Within the image field, line motion may take place in either one of two, generally opposite directions, such as from right-to-left, and left-to-right, where the lines are disposed substantially upright as is pictured specifically in FIGS. 2, 3 and 4A.

Under appropriate control provided by the earlier-mentioned, administrator-input structure and the associated virtual-control structure, and as is suggested by a double-headed, curved arrow 32 in FIG. 3, which arrow curves about an axis shown at 32a, a test administrator may rotate the image field to an infinite number of different angular dispositions about axis 32a.

As will now be explained, a test administrator may choose to implement a test utilizing any one of a variety of manners of presentation of a test image, with all such "manners" being made selectable and useable through previously mentioned virtual-control structure 27. For example, it is entirely possible (a) to change test-image field size, (b) to change the angular orientation, as was just mentioned, of the test field per se, (c) to change line width, line length, and interline spacing either to maintain these two dimensions equal to one another or to differentiate them, (d) to change line and background colors, and (e) to change line-to-background contrast so as to enhance important edge contrast between the edge of a line and the background lying behind the line. It is further possible for the system to be structured in such a fashion that computer 12 is operated to present, during a test, a predetermined, ever-changing test image to the eye.

In the context now of implementation of the invention, and with a test about to occur, a subject is positioned appropriately in front of display device 12a, and is asked to gaze with a single eye at a test image, with the central focus of that gaze being aimed at, and held on, the test image's central dot (previously mentioned), and with the eye which is to be tested moved toward and away from the test image to a point where the previously mentioned lateral image dot disappears from the subject's peripheral vision.

The test image, including all of its parameters, is selected by a test administrator, and is then presented on the screen of display device 12a for viewing, and specifically for projecting upon, and thus illuminating, central field 24b in the eye.

Under these circumstances, if there is no evidence whatsoever, and in fact no condition detectable whatsoever, of macular condition degeneration in the eye being tested, the subject-perceived perception image (block 14) will look substantially like the presented source test image. When asked to report the image perceived, the user will report no change or distortion as a difference between the perception image and the test image.

However, where even early-stage degeneration of macular condition and/or neural pathway transmission functionality has taken place in a test subject's eye, we have observed that the subject under test, with respect to that eye, will report, when requested to do so, a perception image which evidences a change or distortion in relation to the test image.

With attention now directed specifically to FIGS. 4 and 5 in the drawings, FIG. 4B illustrates at 34 (in a perception image 14) such a change, or distortion, which change specifically takes the form of a slight lateral displacement, to the right in this figure, of vertically central portions of several laterally test-image central lines. Such shifting in FIG. 4B includes both linear and wavy lateral distortion. Image 4B is thus an illustration—a manifestation—of degeneration, and even possibly early-stage degeneration, in macular and/or neural pathway physiologic condition(s).

The subject who experiences this FIG. 4B perception image is requested by the test administrator to describe, if any, the presence, character, location, style and outline of the perception image distortion, and is further requested to "draw" the perimeter outline of that distortion. Such drawing may be performed in any convenient manner, such as on a piece of paper, etc., on the screen display of the test image where the associated display screen is of the touch-screen type, on a touch tablet, etc. For illustration purposes herein, display device 12a is a touch-screen-type structure.

FIG. 4C illustrates at 36 such a requested and rendered outline drawing, and FIG. 4D represents at 37 a signal-processed version of that perceived distortion, based upon subject report, created appropriately by computer 12, and rendered so as to indicate certain regional areas within the overall distortion outline of particular interest. For example, distortion "intensity" might be represented by the three differently shaded regions 37a, 37b, 37c within the overall outline of distortion which is pictured in FIG. 4D.

FIGS. 5A and 5B illustrate, respectively, two, different representative kinds of perception image distortions. FIG. 5A illustrates a distortion characterized by a complete absence of central line continuity in the image. FIG. 5B illustrates a kind of ghosting distortion in the perception image. Other kinds of changes and/or distortions in a perception image may also, of course, occur.

We believe that these distortions, and particularly the distortion evidenced at 34 in FIG. 4B, result from a time delay, or a retardation, in either or both in macular response time and the communication of image information between the central field in the tested eye and the brain. In other words, distortion existing in a perception image may not only indicate a certain kind and level of macular dysfunctionality, but may also simultaneously illustrate communication degradation in the neural pathways that exist at certain locations between the eye's central field and the brain.

As has also been mentioned herein, we have observed that these kinds of perception distortions become present and observable via practice of the present invention even at very early stages of macular and/or neural-pathway performance degradation in a person's eye-to-brain physiology.

Shifting attention now to FIG. 6 along with FIG. 5, FIG. 6 further illustrates the earlier-mentioned feedback practice which is made possible in the implementation of the present invention with respect to which information received from an observer who reports a distorted perception image is utilized, under test administrator control, to effect changes in the source image which tend to counterbalance and eliminate perceived distortion. Thus, illustrated by a block internally labeled C in FIG. 6 is a feedback correction input which is supplied by a test administrator to computer 12 through the above-mentioned user-input structure to create a "corrected" source image (block 38) to be delivered to the eye so as, ultimately, to effect a perception image that is more nearly is the same as the originally presented, undistorted test image. Block C is also labeled 20, 22 to indicate its functional relationship to companion structure and methodology pictured in FIG. 1. Block C is referred to herein additionally as correction and feedback structure.

With this practice undertaken, at the conclusion of image adjustment to produce such a corrected image, feedback information may be quantified, as illustrated by block 40 in FIG. 6, to furnish quantitative data regarding macular and/or neural pathway physiologic dysfunctionality which has been detected by practice of the present invention.

Thus, a unique practice, and a system enabling implementation of this practice, for testing, fundamentally, the eye and the eye-to-brain physiology of a subject has been disclosed herein. With regard to the unique methodology of this invention, one way of describing this methodology is to characterize it as being a physiologic test including the steps of (a) illuminating the central field in a subject's eye with a defined-configuration, relative-motion test image, (b) by this illuminating, creating a related, subject-perception image, (c) requesting a subject report describing the observed presence and nature, if any, of a distortion, relative to the test image, in the perception image, and (d) utilizing such a report, assessing a related subject-physiologic condition.

As subsets of this description, and considered independently, the illuminating step of the methodology may include one of (a) preparing the test image to possess a moving zone of light/dark contrast, (b) preparing the test image to possess at least a pair of next-adjacent motion image elements (the illustrated lines herein) having a common edge of juxtaposition which is characterized by contrast, (c) impinging a portion of at least one of the macula and the paramacula in the mentioned central field of the eye with the relevant source test image, (d) performing illumination in a manner consciously avoiding the invocation of any related nystagmus—a condition which will interfere with the utility of test results in most instances, and (e) preparing the test image in the form specifically of a pattern of elongate, spaced, substantially straight and parallel, laterally next-adjacent lines which move within the image in a direction that lies along a path which intersects the lines' respective long axes.

With respect to the general characterization of the invention presented above, a further methodologic step includes adjusting the test image in relation to at least one of (a) line-motion speed, (b) line-motion direction, (c) transverse line width, (d) transverse, next-adjacent line spacing, (e) line brightness, (f) contrast and (g) coloration.

Still another overall way of viewing the methodology of this invention is to view it as being a kinetic method for assessing, in relation to a subject's eye, at least one of (a) disruption of macular metabolic condition and (b) neuron-path malfunction, with this method approach including detecting, relative to a subject-perceived perception image, spatial-differential time-lag in a portion of that perception image which is derived from a predetermined, transversely spatially expansive, plural-moving element test image whose elements are caused to illuminate, and to move in a defined manner transversely relative to, the eye's central field.

Still a further overall way of viewing the methodology of the present invention is to see it as being a kinetic method for detecting, in a subject's eye, disruption therein of macular metabolic condition, including macular degeneration, including the steps of (a) illuminating at least one of the macula and the paramacula in the subject's eye with motion image elements contained in a controlled, externally produced test image having (1) a predetermined stable spatial configuration, and (2), with respect to the motion elements in the image, a defined direction of element motion relative to the eye, (b) by the illuminating step, creating for the subject a related perception image, and (c), during the illuminating and creating steps, requesting report information from the subject which indicates any perception by that subject of a difference existing between the test image and the perception image.

There are various subsets of this view of the invention, in one of which, the requesting step involves seeking information regarding a person's observation of the presence of a perception image distortion which occurs generally along a line that substantially follows the direction of perception-image motion-element motion.

Another subset involves practicing the seeking step just mentioned in such a manner wherein it involves soliciting information relative to image differences, which differences include issues concerning one of (a) waviness, (b) lateral displacement, (c) omission and (d) ghosting.

The just viewpoint-described kinetic method of the invention may further include the step of interpreting any reported difference between test and perception images as a performance deficiency in neuron-path communication initiated from a portion of the central field in the subject's eye, and/or interpreting any such reported difference as a perception time-response deficiency that is associated with the performances of certain portions of the central field in a subject's eye.

Another subset of the methodologic view of the invention now being discussed recognizes that the test and perception images have related lateral boundaries, i.e., the boundaries of the overall field generated by and within the test image, and the report information which is requested from a subject includes information describing generally the shape and location of such a reported difference relative to the lateral boundaries (overall) of the perception image, and which further, in terms of a major step in the methodology, includes utilizing such shape and location information as an identifier of that portion of the eye's central field wherein physiologic dysfunctionality is detected.

Still another view of the methodologic characterization of the invention now being discussed further includes, based upon receipt of reported difference information, adjusting the test image in a feedback fashion so as to diminish, as much as possible, the difference perceived by the subject between the test and the perception images, and thereafter quantifying at least one aspect of that adjusting activity.

From a structural and systemic point of view, the present invention proposes a physiologic, perception-image-distortion, eye-test system which includes (a) motion-image-creation structure for generating a controllable, defined-configuration test image including edge-contrast, relative-motion elements, and subject viewing-position visual marker structure and, (b) image display structure which is operatively connected to the motion-image-creation structure, and which is operable, during the implementation of a physiologic eye test, to display such a test image under subject-test conditions that are defined by the positioning of a test subject in a proper relative positional association with the test image's included marker structure. This systemic view of the invention is one, a bit more specifically, wherein the motion-image-creation structure includes an interactive, user-interface structure that is operable to introduce changes in the test image.

The system of the invention may further include correction and feedback structure which is operatively connected to the motion-image-creation structure and the user-interface structure, and which is operable to effect changes in the test image that are designed to minimize perception-image distortion which may be reported by a test subject.

We claim:

1. A physiologic, perception-image-distortion eye-test system comprising:
   a motion-image-creation structure for generating a controllable, defined-configuration test image including edge-contrast, relative-motion elements and subject viewing-position and viewing-condition visual marker structure, and
   an image display structure operatively connected to said motion-image-creation structure, operable, during the implementation of a physiologic eye test with regard to a particular subject, to display said test image under subject-test conditions that are defined by positioning of a test subject in proper relative positional association with the test image and said marker structure.

2. The system of claim 1, wherein said motion-image-creation structure includes user-interface control structure operable to introduce changes in the test image.

3. The system of claim 2 which further comprises correction and feedback structure operatively connected to said motion-image-creation structure and to said user-interface control structure, operable to effect changes in the test image that are designed to minimize perception-image distortion which may be reported by a test subject.

* * * * *